(12) United States Patent
Hochrein et al.

(10) Patent No.: US 10,058,648 B2
(45) Date of Patent: Aug. 28, 2018

(54) APPARATUS FOR EXTRACORPOREAL BLOOD TREATMENT AND METHOD FOR MONITORING THE FLUID FLOW OF AN EXTRACORPOREAL BLOOD TREATMENT APPARATUS

(75) Inventors: Torsten Hochrein, Knetzgau (DE); Pascal Werner, Uechtelhausen (DE); Sabine Kipp, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1107 days.

(21) Appl. No.: 13/451,062

(22) Filed: Apr. 19, 2012

(65) Prior Publication Data

US 2012/0267290 A1    Oct. 25, 2012

Related U.S. Application Data

(60) Provisional application No. 61/477,655, filed on Apr. 21, 2011.

(30) Foreign Application Priority Data

Apr. 21, 2011 (DE) .................. 10 2011 018 601

(51) Int. Cl.
  *A61M 37/00*   (2006.01)
  *A61M 1/34*    (2006.01)
  *A61M 1/36*    (2006.01)

(52) U.S. Cl.
  CPC ........ *A61M 1/3472* (2013.01); *A61M 1/3486* (2014.02); *A61M 1/367* (2013.01);
  (Continued)

(58) Field of Classification Search
  None
  See application file for complete search history.

(56) References Cited

U.S. PATENT DOCUMENTS 4,657,529 A * 4/1987 Prince ................. A61M 1/3639
                                              128/DIG. 13
5,358,482 A    10/1994 Panzani
(Continued)

FOREIGN PATENT DOCUMENTS

JP    06-063128 A    3/1994
JP    2005-006873 A   1/2005
(Continued)

OTHER PUBLICATIONS

PCT International Search Report and Written Opinion from PCT/EP2012/001594, dated Jul. 13, 2012.
(Continued)

*Primary Examiner* — Michael H. Wilson
*Assistant Examiner* — Katherine A Will
(74) *Attorney, Agent, or Firm* — Kilyk & Bowersox, P.L.L.C.

(57) ABSTRACT

The invention relates to the monitoring of the fluid flow in an apparatus for extracorporeal blood treatment. The device according to the invention and the method according to the invention are based on the fact that, in order to monitor the fluid flow, the change in weight of a collection container is monitored, in which a rinsing fluid is collected during a filling or rinsing phase. The monitoring of the fluid flow according to the invention permits continuous monitoring of the fluid flow both in a treatment mode, in which the blood treatment is carried out, as well as in a filling or rinsing mode, in which the fluid system is filled or rinsed with a fluid.

18 Claims, 1 Drawing Sheet

(52) U.S. Cl.
CPC ........ *A61M 1/3644* (2014.02); *A61M 1/3679* (2013.01); *A61M 1/3496* (2013.01); *A61M 1/3643* (2013.01); *A61M 2205/3393* (2013.01)

(56) References Cited

U.S. PATENT DOCUMENTS

| | | | | |
|---|---|---|---|---|
| 5,910,252 | A * | 6/1999 | Truitt | A61M 1/16 210/103 |
| 6,322,488 | B1 * | 11/2001 | Westberg | A61M 1/38 494/39 |
| 2004/0182783 | A1 | 9/2004 | Walker et al. | |
| 2004/0182787 | A1 | 9/2004 | Chevallet et al. | |
| 2011/0040228 | A1 * | 2/2011 | Radunsky | A61M 1/3413 604/5.04 |

FOREIGN PATENT DOCUMENTS

| | | |
|---|---|---|
| JP | 2006-520635 A | 9/2006 |
| JP | 2007-520248 A | 7/2007 |
| WO | 91/15253 A1 | 10/1991 |
| WO | 91/15253 A2 | 10/1991 |
| WO | 97/05938 A1 | 2/1997 |

OTHER PUBLICATIONS

International Preliminary Report on Patentability (IPRP) dated Oct. 22, 2013 in PCT/EP2012/001594.

* cited by examiner

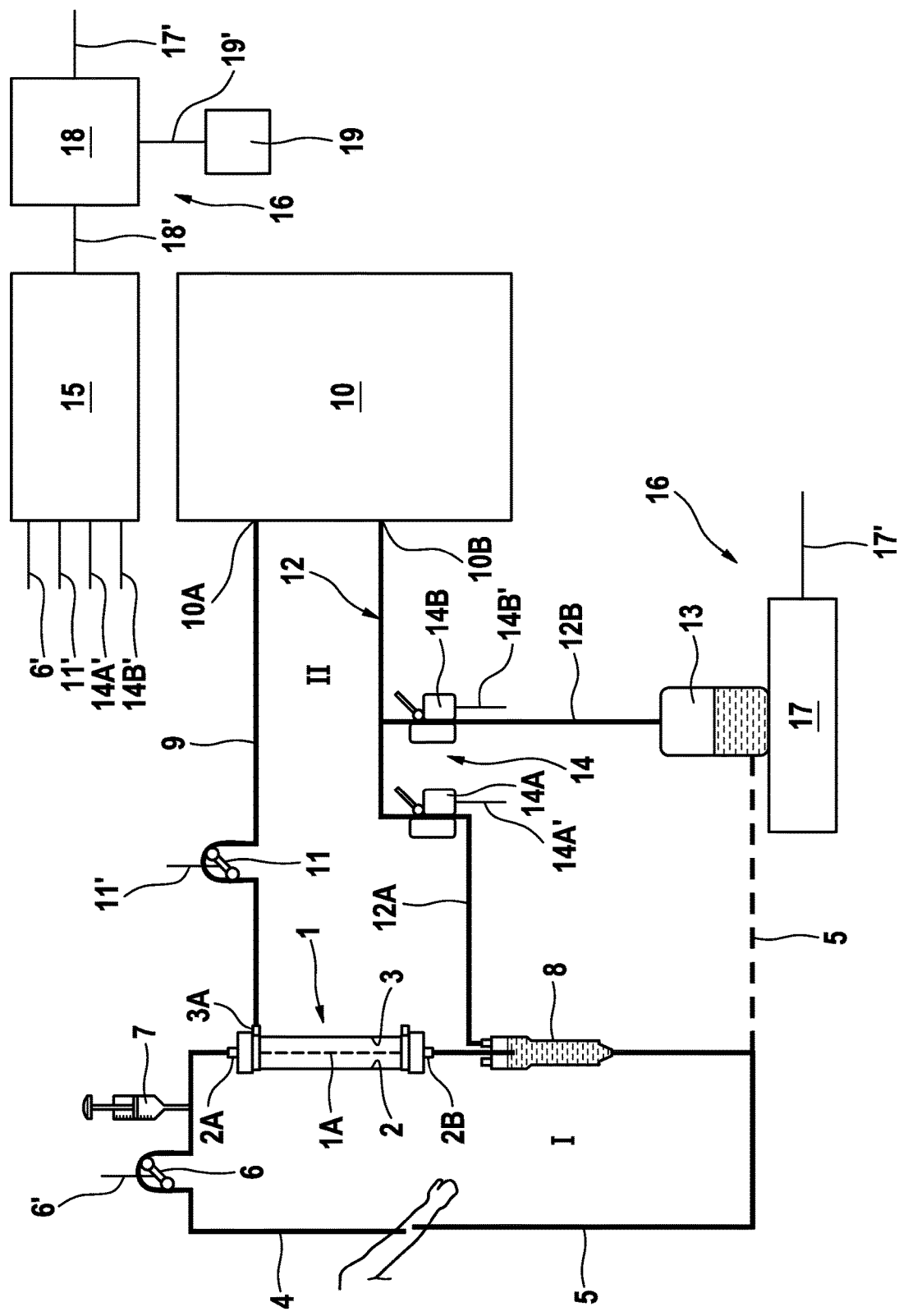

APPARATUS FOR EXTRACORPOREAL BLOOD TREATMENT AND METHOD FOR MONITORING THE FLUID FLOW OF AN EXTRACORPOREAL BLOOD TREATMENT APPARATUS

CROSS-REFERENCE TO RELATED APPLICATIONS

The present application claims priority to, and the benefit of, U.S. Provisional Application 61/477,655 filed on Apr. 21, 2011. The contents of this provisional application is incorporated herein by reference in its entirety. The present application also claims priority to, and the benefit of, German Patent Application DE 10 2011 018 601.8 filed on Apr. 21, 2011. The contents of this foreign application is incorporated herein by reference in its entirety.

FIELD OF THE INVENTION

The invention relates to an apparatus for extracorporeal blood treatment, which comprises a unit for obtaining one or more blood constituents and a treatment unit for treating the obtained blood constituent or constituents. Moreover, the invention relates to a method for monitoring the fluid flow in such an extracorporeal blood treatment apparatus.

BACKGROUND OF THE INVENTION

As therapeutic apheresis, a blood purification procedure is known, wherein blood or blood plasma in an extracorporeal circuit is freed from pathogenic substances. A distinction is made between non-selective plasmapheresis, wherein the plasma is separated from the blood and completely substituted, and selective plasmapheresis, wherein plasma is freed from pathogenic substances by filtration or adsorption. Diseases that are treated with therapeutic apheresis are for example autoimmune diseases. The known extracorporeal blood treatment apparatuses can be used for therapeutic apheresis.

The known extracorporeal blood treatment apparatuses for apheresis comprise a unit for obtaining plasma, in particular a plasma filter, and a treatment unit for treating the obtained plasma, in particular a purification unit comprising one or more filters or adsorbers.

The plasma filter is located in the extracorporeal blood circuit of the blood treatment apparatus. A blood supply line leads from the patient to the inlet of the plasma filter and a blood return line leads from the outlet of the plasma filter to the patient, so that blood removed from the patient can be conveyed through the plasma filter. The plasma obtained in the plasma filter is then conveyed through the purification unit and the purified plasma is again fed to the patient's blood in the extracorporeal blood circuit.

Blood and plasma are conveyed by means of pumps in hose lines, which are filled and rinsed with fluid before the start of the blood treatment. The rinsing solution is collected in a collection container, in particular a bag. In order to avoid contamination by germs, the collection bag remains on the hose line system during the whole treatment, which can last for three to five hours.

In the known blood treatment apparatuses for therapeutic apheresis, the line leading away from the purification unit branches into a first line segment leading to the blood return line and a second line segment leading to the collection container. During the treatment mode, the purified plasma flows through the first line segment to the blood return line, while the second line segment is closed. In the filling and rinsing mode, on the other hand, the rinsing solution is conveyed through the second line segment into the collection bag. The fluid flow is changed over by means of a change-over clamp, into which both line segments of the line leading away from the purification unit are placed.

In the treatment mode, it must be ensured that the purified plasma does not get into the collection bag, whereas in the filling and rinsing mode it must be ensured that the rinsing solution is collected in the collection bag. Monitoring of the correct function of the change-over clamp is therefore required.

Devices for therapeutic apheresis are known, wherein a pressure and clamp test is carried out in order to establish whether the hose line is properly placed in the change-over clamp. Change-over clamps are known which comprise a safety clip, which opens when the hose line is removed or slides out. An alarm is emitted when the safety clip opens.

The monitoring of the weight of containers for making available and collecting fluids during an extracorporeal blood treatment is known, for example as described in WO 91/15253 and U.S. Pat. No. 7,686,778 B2. For example, balances are used for balancing fresh and used dialysing fluid, which is made available and/or collected in a bag. The monitoring of the level of bags is also known in order to detect when they become empty or overflow.

The invention herein is to increase further the reliability of an extracorporeal blood treatment apparatus.

SUMMARY OF THE INVENTION

The device according to the invention and the method according to the invention are based on the fact that, in order to monitor the fluid flow in the line leading away from the blood treatment unit, the change in weight of the collection container is monitored. It is possible to conclude that there is a defective state solely on the basis of the change in weight of the collection container. The monitoring of the fluid flow according to the invention can replace the known monitoring of the function of the change-over clamp. In order to increase the redundancy, however, both safety devices can also be provided.

The monitoring device according to the invention comprises means for determining the weight of the collection container and an evaluation unit, which is constituted such that a change in the weight of the collection container can be ascertained in order to monitor the fluid flow. The means for determining the weight can be a conventional electronic balance, onto which a collection bag can be placed or on which the bag can be suspended.

The monitoring of the fluid flow according to the invention permits continuous monitoring of the fluid flow both in a treatment mode, in which the blood treatment is carried out, as well as in a filling and rinsing mode, in which the fluid system is filled and rinsed with a fluid.

The extracorporeal blood treatment apparatus provides a control unit for selecting the treatment mode or the filling or rinsing mode. In the treatment mode, one or more blood components, in particular blood plasma, are conveyed via the first segment of the line leading away from the blood treatment unit to the blood return line, while in the filling or rinsing mode, fluid, in particular a rinsing fluid, is conveyed by the second segment of the line leading away from the blood treatment unit into the collection container. The evaluation unit monitors the change in the weight of the collection container during the treatment mode or the filling or rinsing mode.

In the case where the control unit selects the treatment mode, the evaluation unit generates a first control signal when an increase in weight is ascertained, preferably in a preset time interval. If an increase in weight is ascertained in the preset time interval, it can be concluded that one or more blood components, in particular blood plasma, have got into the collection container during the treatment mode. This can only be the case when there is a defective fluid flow through the line leading away from the blood treatment unit. Continuous monitoring of the plasma flow is therefore made possible by monitoring the increase in weight, it being ensured that plasma cannot flow away unintentionally into the surroundings, i.e. cannot be discarded into the collection bag during the blood treatment.

In the case where the control unit selects the filling or rinsing mode, the evaluation unit generates a second signal when, after the lapse of a preset time interval after the start of the filling or rinsing mode, an increase in weight is not ascertained, preferably in a preset time interval. If an increase in weight in the preset time interval is not ascertained, it can be concluded that rinsing fluid is not getting into the collection container. A defective state is then again present. The preset time interval is fixed in such a way that the hose lines of the fluid system can be completely filled with rinsing fluid. This is because it is only with complete filling of the hose lines of the fluid system with fluid that an increase in weight of collection bag 13 can be expected. This is however the case after the lapse of the preset time interval.

When the control unit generates the first or second control signal, an acoustic and/or optical alarm can be emitted. The blood treatment apparatus according to the invention provides an alarm unit for this.

It is advantageous if the alarm unit generates a first alarm signal when the first control signal is generated and a second alarm signal when the second control signal is generated, in order that a distinction can be made between the two defective states during the treatment mode or the filling or rinsing mode.

In a particularly preferred embodiment of the invention, the amount of the change in the weight of the collection container in a preset time interval is determined in the filling or rinsing mode, again after the lapse of a preset time interval after the completed filling of the hose lines of the fluid system, and the amount of the change in weight in the preset time interval is compared with a preset threshold value in order to be able to ascertain not only whether the weight increases, but also to be able to ascertain the amount by which the weight increases. The filling of the fluid system, in particular of the plasma circuit, can thus be monitored. After the start of the filling or rinsing mode, it is also possible to monitor whether a continuous increase in weight is established in a preset time interval. Only when this is the case can it be concluded that the fluid system is air-free.

If the increase in weight lies below a preset threshold value, it can be concluded that there is a defective state. For example, it can be concluded that the hose line is not seated properly in the single change-over clamp for changing over the fluid flow or in the two hose clamps.

In a further particularly preferred embodiment, the weight of the collection container is ascertained at the start of the filling or rinsing mode and after completion of the filling or rinsing mode, in order to determine the conveyed volume of fluid in the fluid system, in particular of the plasma circuit. However, this again requires the complete filling of the hose lines of the fluid system with fluid.

The monitoring of the fluid flow on the basis of the weight of the collection container can be used in all blood treatment apparatuses that comprise a unit for obtaining one or more blood constituents and a treatment unit for treating the obtained blood constituent or constituents, wherein the treated blood components are fed back to the blood. It is not important how the unit for obtaining the blood constituents and the treatment unit are constituted. The extracorporeal blood treatment apparatus is, in particular, an apparatus for apheresis, wherein the unit for obtaining one or more blood constituents is a unit for obtaining plasma, in particular a plasma filter, and the blood treatment unit is a unit for freeing the plasma of pathogenic components, for example a purification unit comprising one or more filters or adsorbers.

The means for changing over the fluid flow preferably comprises a first hose clamp for pinching off the first line segment of the line leading away from the blood treatment unit, and a second hose clamp for pinching off the second line segment of the line leading away from the blood treatment unit. Both hose clamps can however also form a unit. For example, it may be a change-over clamp.

BRIEF DESCRIPTION OF THE DRAWINGS

FIG. 1 shows, in a very simplified schematic representation, the main components of the extracorporeal blood treatment apparatus, which comprises a device for monitoring the fluid flow.

DETAILED DESCRIPTION OF THE INVENTION

In one embodiment of the invention, the device for monitoring the fluid flow is a component of the extracorporeal blood treatment apparatus. It can however also be a separate assembly. In the present example of embodiment, the extracorporeal blood treatment apparatus is a device for therapeutic apheresis.

The blood treatment apparatus comprises an extracorporeal blood circuit I, which comprises a unit 1 for obtaining one or more blood constituents. In one embodiment, this unit is a plasma filter 1, which is divided by a semi-permeable membrane 1A into a first chamber 2 and a second chamber 3. A blood supply line 4 leads from the patient to inlet 2A of first chamber 2 of plasma filter 1. A blood return line 5 leads from outlet 2B of first chamber 2 of plasma filter 1 back to the patient.

A blood pump 6, which is incorporated into blood supply line 4, is used to convey the blood from the patient into plasma filter 1. Heparin can be fed upstream of plasma filter 1 to the patient's blood by means of a heparin pump 7 represented solely by way of indication. A drip chamber 8 is incorporated into blood return line 5.

Apart from extracorporeal blood circuit I, the blood treatment apparatus comprises a secondary circuit II, which will be referred to below as plasma circuit II. Plasma circuit II comprises a line 9, which leads away from outlet 3A of second chamber 3 of plasma filter 1 and leads to inlet 10A of blood treatment unit 10. In the present example of embodiment, blood treatment unit 10 represented solely by way of indication in the FIGURE is a purification unit, which comprises one or more filters or adsorbers in order to purify the plasma obtained from the patient's blood in plasma filter 1. The plasma is conveyed from plasma filter 1 to blood treatment unit 10 by means of a plasma pump 11, which is incorporated into line 9.

The purified plasma is fed back to the patient's blood. Leading away from outlet 10B of blood treatment unit 10 is a line 12, which branches into a first line segment 12A and a second line segment 12B. First line segment 12A leads to blood return line 5. In one embodiment, first line segment 12A is connected to drip chamber 8 incorporated into blood return line 5. Second line segment 12B of line 12 leading away from blood treatment unit 10 leads to a container 13 for the collection of fluid, in particular a collection bag.

Lines 4, 5 of extracorporeal blood circuit I and lines 9, 12 of plasma circuit II are hose lines of one or more hose line sets.

Collection bag 13 serves to accommodate a rinsing fluid. For apheresis, bag 13 remains firmly connected to the hose set in order to reduce the risk of contamination by germs.

During the apheresis, the fluid flow in hose line segment 12B of hose line 12 leading to collection bag 13 is interrupted, so that the purified plasma cannot get into collection bag 13. During the filling or rinsing mode, on the other hand, rinsing fluid is discarded through line segment 12B of line 12 into collection bag 13. Moreover, blood return line 5 can be connected to collection bag 13 in the filling and rinsing mode. The connection of blood return line 5 to collection bag 13 is indicated in the FIGURE by a dashed line. When blood return line 5 is connected to collection bag 13, the collection bag is filled in the filling and rinsing mode both via second line segment 12B of line 12 leading away from blood treatment unit 10 as well as via blood return line 5.

The means for changing over fluid flow 14 are represented only schematically in the FIGURE. In the present example of embodiment, they involve two hose clamps 14A, 14B which are operated alternately. Hose line segments 12A and 12B of hose line 12 must be inserted into hose clamps 14A, 14B before the filling or rinsing mode, i.e. before the blood treatment, in order to be able to pinch off respective line segments 12A, 12B.

Moreover, the blood treatment apparatus comprises a central control unit 15, which is connected via control lines 6', 11' to blood pump 6 and plasma pump 11.

Device 16 for monitoring the fluid flow comprises means 17 for weighing collection bag 13, an evaluation unit 18 and an alarm unit 19. Evaluation unit 18 is connected via a data line 18' to central control unit 15 of the blood treatment apparatus, while alarm unit 19 is connected via a data line 19' to evaluation unit 18. Evaluation unit 18 can however also be a component of central control unit 15 of the blood treatment apparatus. Means 17 for weighing collection bag 13 are connected via a data line 17' to evaluation unit 18. Hose clamps 14A, 14B of means 14 for changing over the fluid flow can be manually operated hose clamps. In the present example of embodiment, the hose clamps are operated alternately via control lines 14A', 14B' by central control unit 15.

Central control unit 15 can select a treatment mode and a filling and rinsing mode. In the treatment mode, control unit 15 opens first hose clamp 14A, which is used to pinch off first segment 12A of line 12, and closes second hose clamp 14B, which is used to pinch off second segment 12B of line 12, so that plasma cannot get into collection bag 13. In the filling and rinsing mode, on the other hand, control unit 15 opens second hose clamp 14B, so that rinsing fluid can be discarded into collection bag 13.

Apart from the components described above, the blood treatment apparatus can also comprise further components, for example an anti-coagulation bag and an anti-coagulation pump or further hose clamps, in particular a venous clamp, which however are not represented in the FIGURE.

The mode of functioning of the monitoring device is described in detail below.

It is assumed that central control unit 15 selects the treatment mode. In the treatment mode, it must be ensured that second hose clamp 14B is closed. Moreover, it must be ensured that second segment 12B of line 12 is inserted into second hose clamp 14B. Otherwise, the hose clamp could not pinch off the line segment, so that plasma could get into collection bag 13.

During the blood treatment, evaluation unit 18 continuously receives the signals of means 17 for weighing the weight of the collection bag, in order to ascertain whether the weight is increasing or remaining constant. If evaluation unit 18 detects an increase in weight, a first control signal is generated which is received by alarm unit 19. The alarm unit then emits a first acoustic or optical alarm, which indicates that plasma is getting into the surroundings. The first control signal is also received by central control unit 15, which can carry out an intervention into the machine control. For example, control unit 15 can interrupt the blood treatment. Evaluation unit 18 thus verifies whether the weight of collection container 13 is increasing during the blood treatment. As long as the weight does not increase, a correct operation is ensured.

In the filling or rinsing mode, it must be ensured that second hose clamp 14B is open, so that rinsing fluid is discarded into plasma bag 13 for the complete air-free filling of the entire plasma circuit II. When control unit 15 selects the filling and rinsing mode, evaluation unit 18 again monitors the weight of collection bag 13. Evaluation unit 18 generates a second control signal when an increase in weight is not ascertained after the lapse of a preset time interval after the start of the filling and rinsing mode. In this case, second hose clamp 14B is closed. The preset time interval is fixed in such a way that the fluid system can be completely filled with rinsing fluid. This is because, in practice, the hose lines of the fluid system are not completely filled with fluid before the filling and rinsing mode or at the start of the filling and rinsing phase, since air is present at least in parts of the fluid system. Only when the hose lines of the fluid system are completely filled with fluid can an increase in weight of collection bag 13 be expected. This is the case, however, after the lapse of the preset time interval.

When the second control signal is generated, alarm unit 19 emits a second acoustic and/or optical alarm signal, which indicates a defective state. Control unit 15 also receives the second control signal, in order to be able to carry out an intervention into the machine control. For example, the control unit can interrupt the filling or rinsing mode.

In the present example of embodiment, evaluation unit 18 monitors not only whether an increase in weight is present, but also monitors the amount of the increase in weight per unit of time. It determines the amount of the change in weight of collection bag 13 in a preset time interval and compares the amount of the change in weight in the preset time interval with a preset value. If the amount of the change in weight in the preset time interval is less than a preset threshold value, a third control signal is generated, which can trigger a third alarm and a further intervention into the machine control. It is thus possible to monitor the flow of the rinsing fluid into collection bag 13. If, in the case of a defective state, the fluid flow falls below a setpoint value, the otherwise continuous increase in the specific weight of collection bag 13 declines, so that the amount of the change in weight falls below the preset value. In the case of the monitoring of the amount of the increase in weight per unit of time, the generation of the third control signal also does not take place until after the lapse of a preset time interval after the start of the filling or rinsing mode, which is fixed in such a way that complete filling of the fluid system is to be expected in this time interval.

Apart from the monitoring of the increase in weight of the collection bag in a specific preset time interval of the filling or rinsing mode, evaluation unit 18 can in principle also provide for monitoring of the increase in weight during the whole filling and rinsing phase, although this requires that the fluid system is previously completely filled with fluid before the monitoring starts. For this purpose, the evaluation unit determines the weight of collection container 13 at the start of the filling or rinsing mode at a time at which the fluid system is completely filled with fluid, and after completion of the filling and rinsing mode. Evaluation unit 18 then ascertains the conveyed volume of fluid in plasma circuit II from the difference in weight of collection bag 13 before the start and after completion of the filling or rinsing mode. For the calculation of the required fluid volume, the specific weight of the rinsing fluid is stored in a memory of evaluation unit 18. If the measured fluid volume deviates from the actual fluid volume of the hose system, evaluation unit 18 can again generate a signal which indicates a defective state and can generate an alarm.

The invention claimed is:

1. An apparatus for extracorporeal blood treatment comprising:
   a blood supply line leading to a unit configured to obtain at least one blood constituent;
   a blood return line leading away from the unit configured to obtain the at least one blood constituent;
   a fluid circuit comprising a treatment supply line and a treatment return line, the treatment supply line leading away from the unit configured to obtain the at least one blood constituent and leading to a treatment unit configured to treat the obtained at least one blood constituent, the treatment return line leading away from the treatment unit and comprising a first line segment leading to the blood return line and a second line segment leading to a collection container configured to collect fluid during a filling or rinsing mode;
   a changing arrangement configured to change over fluid flow between a first direction in which fluid flows through the first line segment and not through the second line segment during a treatment mode, and a second direction in which fluid flows through the second line segment and not through the first line segment during the filling or rinsing mode; and
   a monitoring device configured to monitor the fluid flow through the first line segment or the second line segment, wherein the monitoring device comprises:
      a weight arrangement configured to determine a weight of the collection container;
      an evaluation unit configured to determine whether a preset time interval from a start of the filling or rinsing mode has lapsed, and determine whether a defective state occurs based on an absence of a change in the weight of the collection container during the filling or rinsing mode after determining that the preset time interval has lapsed, the preset time interval being fixed and of sufficient duration to enable complete air-free filling of the entire fluid circuit with a rinsing fluid during the filling or rinsing mode; and
      a control unit configured to (1) select the filling or rinsing mode in which fluid is conveyed into the collection container via the second line segment, and (2) generate a second control signal if an increase in the weight of the collection container is not determined by the evaluation unit after a lapse of the preset time interval from a start of the filling or rinsing mode.

2. The apparatus according to claim 1, wherein the evaluation unit is configured to:
   determine an amount of the change in the weight of the collection container in the preset time interval;
   compare the amount of the change in the weight with a preset value; and
   generate the second control signal if the amount of the change in the weight is less than the preset value.

3. The apparatus according to claim 1, wherein the evaluation unit is configured to determine the weight of the collection container at the start of the filling or rinsing mode and after completion of the filling or rinsing mode.

4. The apparatus according to claim 3, wherein the evaluation unit is configured to determine a conveyed volume of fluid in the fluid system from a difference in the weight of the collection container at the start of the filling or rinsing mode and after completion of the filling or rinsing mode.

5. The apparatus according to claim 1, further comprising:
   an alarm unit coupled to the evaluation unit, the alarm unit configured to generate at least one of an acoustic or optical alarm when the evaluation unit generates a control signal.

6. The apparatus according to claim 1, wherein the extracorporeal blood treatment apparatus is an apheresis apparatus, and wherein the unit configured to obtain the at least one blood constituent is a plasma unit.

7. The apparatus according to claim 6, wherein the plasma unit includes a plasma filter.

8. The apparatus according to claim 6, wherein the treatment unit is configured to free plasma from pathogenic components.

9. The apparatus according to claim 1, wherein the arrangement configured to change over the fluid flow comprises:
   a first hose clamp configured to pinch off the first line segment; and
   a second hose clamp configured to pinch off the second line segment.

10. A method for monitoring fluid flow in an apparatus for extracorporeal blood treatment, wherein the apparatus for extracorporeal blood treatment comprises: a blood supply line leading to a unit configured to obtain at least one blood constituent; a blood return line leading away from the unit configured to obtain the at least one blood constituent; a fluid circuit comprising a treatment supply line and a treatment return line, the treatment supply line leading away from the unit configured to obtain the at least one blood constituent and leading to a treatment unit configured to treat the obtained at least one blood constituent, the treatment return line leading away from the treatment unit and comprising a first line segment leading to the blood return line and a second line segment leading to a collection container configured to collect fluid during a filling or rinsing mode; a changing arrangement configured to change over fluid flow between a first direction in which fluid flows through the first line segment and not through the second line segment during a treatment mode, and a second direction in which fluid flows through the second line segment and not through the first line segment during the filling or rinsing mode; a monitoring device configured to monitor the fluid flow through the first line segment or the second line segment and including a control unit configured to select the filling or rinsing mode in which fluid is conveyed into the collection container via the second line segment, wherein the method comprises:

determining whether a preset time interval from the start of the filling or rinsing mode has lapsed; and determining whether a defective state occurs based on an absence of a change in weight of the collection container during the filling or rinsing mode after determining that the preset time interval has lapsed, the preset time interval being fixed in such a way that sufficient time is allowed for the complete air-free filling of the entire fluid circuit with rinsing fluid during the filling or rinsing mode, before determining whether or not there is an increase in the weight of the collection container.

11. The method according to claim 10, further comprising:

comparing an amount of the change in the weight in the preset time interval with a preset value;

determining the presence of the defective state if the amount of the change in the weight is less than the preset value.

12. The method according to claim 10, wherein the weight of the collection container is measured at the start of the filling or rinsing mode and after completion of the filling or rinsing mode.

13. The method according to claim 12, wherein a conveyed volume of fluid in the fluid system is determined from a difference in the weight of the collection container at the start of the filling or rinsing mode and after completion of the filling or rinsing mode.

14. The method according to claim 10, wherein at least one of an acoustic or optical alarm is emitted after a presence of a defective state is determined.

15. The method according to claim 10, wherein the extracorporeal blood treatment apparatus is an apheresis apparatus, wherein the unit configured to obtain the at least one blood constituent is a plasma unit, wherein the plasma unit includes a plasma filter, and the treatment unit is configured to free plasma from pathogenic components.

16. The apparatus according to claim 1, wherein the evaluation unit is further configured to determine the defective state based on a change in weight of the collection container during the treatment mode.

17. An apparatus for extracorporeal blood treatment comprising:

a blood supply line leading to a unit configured to obtain at least one blood constituent;

a blood return line leading away from the unit configured to obtain the at least one blood constituent;

a fluid circuit comprising a treatment supply line and a treatment return line, the treatment supply line leading away from the unit configured to obtain the at least one blood constituent and leading to a treatment unit configured to treat the obtained at least one blood constituent, the treatment return line leading away from the treatment unit and comprising a first line segment leading to the blood return line and a second line segment leading to a collection container configured to collect fluid during a filling or rinsing mode;

a changing arrangement configured to change over fluid flow between a first direction in which fluid flows through the first line segment and not through the second line segment during a treatment mode, and a second direction in which fluid flows through the second line segment and not through the first line segment during the filling or rinsing mode; and a monitoring device configured to monitor the fluid flow through the first line segment or the second line segment, wherein the monitoring device comprises:

a weight arrangement configured to determine a weight of the collection container;

an evaluation unit configured to determine: (1) whether a preset time interval from the start of the filling or rinsing mode has lapsed, (2) whether a defective state occurs in the treatment mode based on a presence of a change in the weight of the collection container during the treatment mode, and (3) whether a defective state occurs in the filling or rinsing mode based on an absence of a change in the weight of the collection container during the filling or rinsing mode after determining that the preset time interval has lapsed, the preset time interval being fixed and of sufficient duration to enable complete air-free filling of the entire fluid circuit with a rinsing fluid during the filling or rinsing mode; and a control unit, the control unit being (a) configured to select the treatment mode in which at least one blood component is conveyed to the blood return line via the first line segment, wherein, if an increase in the weight of the collection container is determined by the evaluation unit, a first control signal is generated, and (b) configured to select the filling or rinsing mode in which fluid is conveyed into the collection container via the second line segment, wherein, if an increase in the weight of the collection container is not determined by the evaluation unit, after a lapse of the preset time interval from the start of the filling or rinsing mode, a second control signal is generated.

18. A method for monitoring fluid flow in an apparatus for extracorporeal blood treatment, wherein the apparatus for extracorporeal blood treatment comprises: a blood supply line leading to a unit configured to obtain at least one blood constituent; a blood return line leading away from the unit configured to obtain the at least one blood constituent; a fluid circuit comprising a treatment supply line and a treatment return line, the treatment supply line leading away from the unit configured to obtain the at least one blood constituent and leading to a treatment unit configured to treat the obtained at least one blood constituent, the treatment return line leading away from the treatment unit and comprising a first line segment leading to the blood return line and a second line segment leading to a collection container configured to collect fluid during a filling or rinsing mode; a changing arrangement configured to change over fluid flow between a first direction in which fluid flows through the first line segment and not through the second line segment during a treatment mode, and a second direction in which fluid flows through the second line segment and not through the first line segment during the filling or rinsing mode; a monitoring device configured to monitor the fluid flow through the first line segment or the second line segment and including a control unit configured to select the filling or rinsing mode in which fluid is conveyed into the collection container via the second line segment, wherein the method comprises:

determining whether a preset time interval from the start of the filling or rinsing mode has lapsed, the preset time interval being fixed and of sufficient duration to enable complete air-free filling of the entire fluid circuit with a rinsing fluid during the filling or rinsing mode;

determining whether a defective state occurs in the treatment mode based on a presence of a change in the weight of the collection container during the treatment mode and to determine whether a defective state occurs in the filling or rinsing mode based on an absence of a change in weight of the collection container during the filling or rinsing mode after a lapse of the preset interval from the start of the filling or rinsing mode;

generating a first control signal if (i) the control unit selects the treatment mode in which at least one blood component is conveyed to the blood return line via the first line segment, and (ii) an increase in the weight of the collection container is determined; and generating a second control signal if (i) the control unit selects the filling or rinsing mode in which fluid is conveyed into the collection container via the second line segment, and (ii) an increase in the weight of the collection container is not determined after a lapse of the preset interval from the start of the filling or rinsing mode.

* * * * *